United States Patent [19]
Soppet et al.

[11] Patent Number: 5,776,729
[45] Date of Patent: Jul. 7, 1998

[54] HUMAN G-PROTEIN RECEPTOR HGBER32

[75] Inventors: Daniel R. Soppet, Centreville, Va.; Yi Li, Gaithersburg, Md.; Craig A. Rosen, Laytonsville, Md.; Steven M. Ruben, Olney, Md.

[73] Assignee: Human Genome Sciences, Inc., Rockville, Md.

[21] Appl. No.: 461,244

[22] Filed: Jun. 5, 1995

[51] Int. Cl.$^6$ ............................ C12N 15/00; C12N 15/63; C12N 15/85; C07H 21/04

[52] U.S. Cl. ................ 435/69.1; 435/272.3; 435/320.1; 435/325; 536/23.5

[58] Field of Search ..................... 536/23.5; 435/272.3, 435/320.1, 240.2, 69.1, 6, 325

[56] References Cited

FOREIGN PATENT DOCUMENTS

| 9411504 | 5/1994 | WIPO . |
| 9519436 | 7/1995 | WIPO . |

OTHER PUBLICATIONS

Zaballos et al. (1996) Biochem. Biophys. Res. Comm. 227:846–853.
Napolitano et al. (1996) J. Immunol. 157:2759–2763.
Killary et al. PNAS (1992 Nov. 15) 89(22): 10877–10881.
Proc. of the Nat'l. Acad. of Science, vol. 87, issued Apr. 1990, et al., pp. 3052 to 3056.
Science, vol. 244, issued May 5, 1989, Libert, et al., pp. 568 to 572.
Febs Letters, vol. 271, No. 1,2, issued Oct. 1990, Eva, et al., pp. 81 to 84.
The Journal of Biological Chemistry, vol. 265, No. 16, issued Jun. 5, 1990, Hla, et al., pp. 9308 to 9316.
Febs Letters, vol. 284, No. 2, issued Jun. 1991, Meyerhof, et al., pp. 155 to 160.

*Primary Examiner*—Lisa B. Arthur
*Attorney, Agent, or Firm*—Elliot M. Olstein; J. G. Mullins

[57] ABSTRACT

Human G-protein coupled receptor polypeptides and DNA (RNA) encoding such polypeptides and a procedure for producing such polypeptides by recombinant techniques is disclosed. Also disclosed were methods for utilizing such polypeptides for identifying antagonists and agonists to such polypeptides and methods of using the agonists and antagonists therapeutically to treat conditions related to the underexpression and overexpression of the G-protein coupled receptor polypeptides, respectively. Also disclosed are diagnostic methods for detecting a mutation in the G-protein coupled receptor nucleic acid sequences and an altered level of the soluble form of the receptors.

21 Claims, 10 Drawing Sheets

FIG. 1A

```
                              10                    20                    30                    40                    50
  1   CCTCTTTGGGGTCCAAGTGAATCCTTCTGCCTCAGCCTCCTGAGTAGCTAGGATTACAGG                                                          60
                              70                    80                    90                   100                   110
 61   CATGCACCCGCCATGCCCGGCTAATTTTTGTAATTTTTAGTAGAGACGGGGTTTCCCCAT                                                          120
                             130                   140                   150                   160                   170
121   GTTGCCAAGGCTGGTCTTGAACCCCTGACCTCAGGTGATCTGCCTCACCTTGGCCTCCCA                                                          180
                             190                   200                   210                   220                   230
181   AAGTGCTAGGATTACAGGCATGAGCCACAGCTCCCGGTCTATCATTTAACCTTAATTACA                                                          240
                             250                   260                   270                   280                   290
241   TCTTTAAAGGCCCAAATAGTCTCACCCACTCCAAATAGTCACACCCACACGGAGGTTGA                                                           300
                             310                   320                   330                   340                   350
301   GCACTTCAACACATGAATTTGGGGAGGACACAGTTCAGTCCATAACATCCCCTAATTTT                                                           360
                             370                   380                   390                   400                   410
361   TAAAAAATAAAAATGTTTTAAGGAGTGAATGTCTTTATGTGTCTCTGTGACCAGGTCC                                                            420
                             430                   440                   450                   460                   470
421   CGCTGCCTTGATGGATTATACACTTGACCTCAGTGTGACAACAGTGACCGACTACTA                                                             480
  1    M  D  Y  T  L  D  L  S  V  T  T  V  T  D  Y  Y  Y                                                                   17
```

FIG. 1B

```
                         510                           530
             490                          520                          540
481  CCTGATATCTTCTCAAGCCCCTGTGATGCGGAACTTATTCAGACAAATGGCAAGTTGCT       540
 18   P  D  I  F  S  S  P  C  D  A  E  L  I  Q  T  N  G  K  L  L       37

550          570            590
                          560                          600
541  CCTTGCTGTGTCTTTTATTGCCTCCTGTTTGTATTCAGTCTTCTGGGAAACAGCCTGGTCAT    600
 38   L  A  V  F  Y  C  L  L  F  V  F  S  L  L  G  N  S  L  V  I      57

610          630            650
                          620                          660
601  CCTGGTCCTTGTGGTCTGCAAGAAGCTGAGGAGCATCACAGATGTATACCTTCTTAACCT      660
 58   L  V  L  V  V  C  K  K  L  R  S  I  T  D  V  Y  L  L  N  L      77

670          690            710
                          680                          720
661  GGCCCTGTCTGACCTGCTTTTTGCTCGTGCCTTCCCCTTTCAGACTTACTATCTGCTGGA     720
 78   A  L  S  D  L  F  A  R  A  F  P  F  Q  T  Y  Y  L  L  D         97

730          750            770
                          740                          780
721  CCAGTGGGTGTTTGGGACTGTAATGTGCAAAGTGGTGTCTGGCTTTATTACATTGGCTT      780
 98   Q  W  V  F  G  T  V  M  C  K  V  V  S  G  F  Y  Y  I  G  F     117

790          810            830
                          800                          840
781  CTACAGCAGCATGTTTTTCATCACCCTCATGAGTGTGGACAGGTACCTGGCTGTTGTCCA     840
118   Y  S  S  M  F  F  I  T  L  M  S  V  D  R  Y  L  A  V  V  H     137
```

FIG. 1C

```
                      850                          870                           890
 841  TGCCGTGTATGCCCTAAAGGTGAGGACGATCAGGATGGGCACAACGCTGTGCTGGCAGT   900
 138    A  V  Y  A  L  K  V  R  T  I  R  M  G  T  T  L  C  L  A  V    157

910                          930                           950
 901  ATGGCTAACCGCCATTATGGCTACCATCCCATTGCTAGTGTTTACCAAGTGGCCTCTGA    960
 158    W  L  T  A  I  M  A  T  I  P  L  L  V  F  Y  Q  V  A  S  E    177

970                          990                          1010
 961  AGATGGTGTTCTACAGTGTTATTCATTTTACAATCAACAGACTTTGAAGTGGAAGATCTT  1020
 178    D  G  V  L  Q  C  Y  S  F  Y  N  Q  Q  T  L  K  W  K  I  F    197

1030                         1050                          1070
1021  CACCAACTTCAAAATGAACATTTTAGGCTTGTTGATCCCATTCACCATCTTTATGTTCTG  1080
 198    T  N  F  K  M  N  I  L  G  L  L  I  P  F  T  I  F  M  F  C    217

1090                         1110                          1130
1081  CTACATTAAAATCCTGCACCAGTGTCAAAACCACAACAAGACCAAGGCCAT           1140
 218    Y  I  K  I  L  H  Q  L  K  R  C  Q  N  H  N  K  T  K  A  I    237

1150                         1170                          1190
1141  CAGGTTGGTCATTGTGGTCATTGCATCTTTACTTTTCTGGGTCCCATTCAACGTGGT    1200
 238    R  L  V  L  I  V  V  I  A  S  L  F  W  V  P  F  N  V  V       257
```

FIG. 1D

```
      1210            1230              1250
1201 TCTTTCCTCACTTCCTTGCACAGTATGCACATCTTGGATGGATGTAGCATAAGCCAACA 1260
 258  L  F  L  T  S  L  H  S  M  H  I  L  D  G  C  S  I  S  Q  Q  277

1270            1290              1310
1261 GCTGACTTATGCCACCCATGTCACAGAAATCATTTCCTTACTCACTGCTGTGTGAACCC 1320
 278  L  T  Y  A  T  H  V  T  E  I  I  S  F  T  H  C  C  V  N  P  297

1330            1350              1370
1321 TGTTATCTATGCTTTTGTTGGGGAGAAGTTCAAGAAACACCTCTCAGAAATATTTCAGAA 1380
 298  V  I  Y  A  F  V  G  E  K  F  K  K  H  L  S  E  I  F  Q  K  317

1390            1410              1430
1381 AAGTTGCAGGCAAATCTTCAACTACCTAGGAAGACAAATGCTAGGGAGAGCTGTGAAAA 1440
 318  S  C  R  Q  I  F  N  Y  L  G  R  Q  M  P  R  E  S  C  E  K  337

1450            1470              1490
1441 GTCATCATCCTGCCAGCAGGACTCCTCCCGTTCCTCCAGCGTAGACTACATTTGGGAGGA 1500
 338  S  S  S  C  Q  Q  D  S  S  R  S  S  S  V  D  Y  I  W  E  D  357

1510            1530              1550
1501 TCAATGAAGACTAAATATTAAAAACATTTNCTTGAATGGNATGTAGTAGCAGNGGAGCA 1560
 358  Q  *                                                        358

1570
1561 AAGGTGTGGGTGTGTGAAAGGTTTCCAA 1586
```

FIG. 3A

BESTFIT of: hgb32.pep  check: 6268  from: 1  to: 359

TRANSLATE of: hgb32 check: 29 from: 431 to: 1530 generated symbols 1 to: 366.

to: u03905.pep  check: 4236  from: 1  to: 400

TRANSLATE of: u03905.gb_pr check: 5878 from: 3 to: 1979 generated symbols 1 to: 659.
LOCUS      HSU03905      1979 bp    mRNA            PRI       17-APR-1994
DEFINITION  Human monocyte chemoattractant protein 1 receptor (MCP-1b) alternatively spliced mRNA, complete cds.
ACCESSION   U03905 . . .

Symbol comparison table: /gcg/gcgcore/data/rundata/swgappep.cmp
CompCheck: 1254

| | | | |
|---|---|---|---|
| Gap Weight: | 3.000 | Average Match: | 0.540 |
| Length Weight: | 0.100 | Average Mismatch: | -0.396 |
| Quality: | 281.4 | Length: | 356 |
| Ratio: | 0.799 | Gaps: | 4 |
| Percent Similarity: | 64.470 | Percent Identity: | 40.401 |

FIG. 3B

```
hgb32.pep x u03905.pep      April 6, 1995  14:31  ..

.         .         .         .         .         .
  6 DLSVTTVTDYYYPDIFSSPCDAELIQTNGKLLLAVFYCLLFVSLLGNSL  55
    :.:..:: .::.    |  ::.||.  |::.::|:|:::::||  |
 40 NESGEEVTTFFDYD.YGAPCHKFDVKQIGAQLLPPLYSLVFIFGFVGNML  88

.         .         .         .         .
 56 VILVLVVCKKLRSITDVYLLNLALSDLLFARAFPPFQTYYLLDQWVFGTVM 105
    |:|:.||||.||||:|||||:||||:||||  .:|.  ::|||||..|
 89 VVLILINCKKLKCLTDIYLLNLAISDLLFLITLPLWAHSAANEWVFGNAM 138

.         .         .         .         .
106 CKVVSGFYYIGFYSSMFFITLMSVDRYLAVVHAVYYALKVRTIRMGTTLCL 155
    ||...:|||..|::|||||.|.:::||||||||.:|.||.:|:.:|..::
139 CKLFTGLYHIGYFGGIFFIILLTIDRYLAIVHAVFALKARTVTFGVVTSV 188

.         .         .         .         .
156 AVWLTAIMATIPLLVFYQVASEDGVLQCYSFYNQQTLKWKIFTNFKMNIL 205
    .||.:|:.:|  .:||:|  .||:.  .|::.  ::  |.  :||:|||
189 ITWLVAVFASVPGIIFTKCQKEDSVYVCGPYFPRG...WNNFHTIMRNIL 235
```

FIG. 3C

```
206 GLLIPFTIFMFCYIKILHQLKRCQNHNK..TKAIRLVLIVVIASLLFWVPF 254
    ||::|:  |:::||  ||. | ||.|..|   :|||:::::|. :|||.|:
236 GLVLPLLIMVICYSGILKTLLRCRNEKKRHRAVRVIFTIMIVYFLFWTPY 285

255 NVVLFLTSLHSMHILDGCSISQQLTYATHVTEIISFTHCCVNPVIYAFVG 304
    |:|::|..: :::   |.|.   ||. ||:|||.:::|||||:||||||
286 NIVILLNTFQEFFGLSNCESTSQLDQATQVTETLGMTHCCINPIIYAFVG 335

305 EKFKKHLSEIFQKSCRQIFNYLGRQMPRESCEKSSSSCQQDSS..RSSSVD 352
    |||::||.|:| .|.  :|  .: ||..: || .:.: ..:.  .:.
336 EKFRRYLSVFFRKHITKRFCKQCPVFYRETVDGVTSTNTPSTGEQEVSAG 385

353 YIWEDQ 358
     |:|
386 L*NEEQ 391
```

FIG. 4

```
1    MDYTLDLSVITVIDYYYPDIFSSPCDAELIQINGKLLLAVFYCLLFVSLLGNSLVILVLVCKKLRSITDVYLL    75
                                   TM1
76   NLALSDLLFARAFPPQTYYLLDQWFGTVMCKVVSGFYYIGFYSSMFFITLMSVDRYLAVVHAVYALKVRTIRMG   150
         TM2                              TM3
151  TTLCIAVWLTAIMATIPLLVFYQVASEDGVLQCYSFYNQQTLKWKIFTNFKMNILGLLIPFTIFMFCYIKILHQL  225
                       TM4                                 TM5
226  KRQQNHNKTKAIRLVLIVVIASLLFWPFNVLFLTSLHSMHILDGCSISQQLTYATHVTEIISFTHCCVNPVTY   300
                   TM6                                    TM7
301  AFVGEKFKKHLSEIFQKSCRQIFNYLGRQMPRESCEKSSSCQQDSSRSSSVDYIWEDQ                  358
```

HUMAN G-PROTEIN RECEPTOR HGBER32

BACKGROUND OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a human 7-transmembrane receptor. The transmembrane receptor is a G-protein coupled receptor. More particularly, the 7-transmembrane receptor has been putatively identified as a G-protein chemokine receptor, sometimes hereinafter referred to as "HGBER32". The invention also relates to inhibiting the action of such polypeptides.

It is well established that many medically significant biological processes are mediated by proteins participating in signal transduction pathways that involve G-proteins and/or second messengers, e.g., cAMP (Lefkowitz, Nature, 351:353–354 (1991)). Herein these proteins are referred to as proteins participating in pathways with G-proteins or PPG proteins. Some examples of these proteins include the GPC receptors, such as those for adrenergic agents and dopamine (Kobilka, B. K., et al., PNAS, 84:46–50 (1987); Kobilka, B. K., et al., Science, 238:650–656 (1987); Bunzow, J. R., et al., Nature, 336:783–787 (1988)). G-proteins themselves, effector proteins, e.g., phospholipase C, adenyl cyclase, and phosphodiesterase, and actuator proteins, e.g., protein kinase A and protein kinase C (Simon, M. I., et al., Science, 252:802–8 (1991)).

For example, in one form of signal transduction, the effect of hormone binding is activation of an enzyme, adenylate cyclase, inside the cell. Enzyme activation by hormones is dependent on the presence of the nucleotide GTP, and GTP also influences hormone binding. A G-protein connects the hormone receptors to adenylate cyclase. G-protein was shown to exchange GTP for bound GDP when activated by hormone receptors. The GTP-carrying form then binds to an activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuroreceptors.

G-protein coupled receptors have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include calcitonin, adrenergic, endothelin, cAMP, adenosine, muscarinic, acetylcholine, serotonin, histamine, thrombin, kinin, follicle stimulating hormone, opsins, endothelial differentiation gene-1 receptor and rhodopsins, odorant, cytomegalovirus receptors, etc.

Most G-protein coupled receptors have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 (the intracellular loop between TM3 and TM4) has been implicated in signal transduction.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the β-adrenoreceptor, phosphorylation by protein kinase A and/or specific receptor kinases mediates receptor desensitization.

The ligand binding sites of G-protein coupled receptors are believed to comprise a hydrophilic socket formed by several G-protein coupled receptors transmembrane domains, which socket is surrounded by hydrophobic residues of the G-protein coupled receptors. The hydrophilic side of each G-protein coupled receptor transmembrane helix is postulated to face inward and form the polar ligand binding site. TM3 has been implicated in several G-protein coupled receptors as having a ligand binding site, such as including the TM3 aspartate residue. Additionally, TM5 serines, a TM6 asparagine and TM6 or TM7 phenylalanines or tyrosines are also implicated in ligand binding. Furthermore, the extracellular hydrophilic domains have also been shown to have a role in ligand binding.

G-protein coupled receptors can be intracellularly coupled by heterotrimeric G-proteins to various intracellular enzymes, ion channels and transporters (see, Johnson et al., Endoc., Rev., 10:317–331 (1989)). Different G-protein α-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors. G-protein coupled receptors are found in numerous sites within a mammalian host.

SUMMARY OF THE INVENTION

In accordance with one aspect of the present invention, there are provided novel polypeptides as well as biologically active and diagnostically or therapeutically useful fragments and derivatives thereof. The polypeptides of the present invention are of human origin.

In accordance with another aspect of the present invention, there are provided isolated nucleic acid molecules encoding the polypeptide of the present invention including mRNAs, DNAs, cDNAs, genomic DNA as well as antisense analogs thereof and biologically active and diagnostically or therapeutically useful fragments thereof.

In accordance with a further aspect of the present invention, there is provided a process for producing such polypeptides by recombinant techniques which comprises culturing recombinant prokaryotic and/or eukaryotic host cells, containing a nucleic acid sequence encoding a polypeptide of the present invention, under conditions promoting expression of said polypeptide and subsequent recovery of said polypeptide.

In accordance with yet a further aspect of the present invention, there are provided antibodies against such polypeptides.

In accordance with another aspect of the present invention there are provided methods of screening for compounds which bind to and activate or inhibit activation of the receptor polypeptides of the present invention and for receptor ligands.

3

In accordance with still another embodiment of the present invention there is provided a process of using such activating compounds to stimulate the receptor polypeptide of the present invention for the treatment of conditions related to the under-expression of the G-protein coupled receptors.

In accordance with another aspect of the present invention there is provided a process of using such inhibiting compounds for treating conditions associated with over-expression of the G-protein coupled receptors.

In accordance with yet another aspect of the present invention there is provided non-naturally occurring synthetic, isolated and/or recombinant G-protein coupled receptor polypeptides which are fragments, consensus fragments and/or sequences having conservative amino acid substitutions, of at least one transmembrane domain of the G-protein coupled receptor of the present invention, such that the receptor may bind G-protein coupled receptor ligands, or which may also modulate, quantitatively or qualitatively, G-protein coupled receptor ligand binding.

In accordance with still another aspect of the present invention there are provided synthetic or recombinant G-protein coupled receptor polypeptides, conservative substitution and derivatives thereof, antibodies, anti-idiotype antibodies, compositions and methods that can be useful as potential modulators of G-protein coupled receptor function, by binding to ligands or modulating ligand binding, due to their expected biological properties, which may be used in diagnostic, therapeutic and/or research applications.

It is still another object of the present invention to provide synthetic, isolated or recombinant polypeptides which are designed to inhibit or mimic various G-protein coupled receptors or fragments thereof, as receptor types and subtypes.

In accordance with yet a further aspect of the present invention, there is also provided diagnostic probes comprising nucleic acid molecules of sufficient length to specifically hybridize to the nucleic acid sequences of the present invention.

In accordance with yet another object of the present invention, there is provided a diagnostic assay for detecting a disease or susceptibility to a disease related to a mutation in a nucleic acid sequence of the present invention.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A, 1B, 1C, 1D collectively, show the cDNA sequence (SEQ ID NO:1) and the corresponding deduced amino acid sequence (SEQ ID NO:2) of the HGBER32 G-protein coupled receptor of the present invention. The standard one-letter abbreviation for amino acids is used.

FIGS. 3A, 3B and 3C, collectively, illustrate an amino acid alignment of the G-protein coupled receptor of the present invention (HGBER32) beginning at amino acid 6 (residues 6-355 of SEQ ID NO:2) and human monocyte chemoattractant protein 1 receptor (MCP-1b) beginning at amino acid 40 (SEQ ID NO:3). Line matches indicate identical amino acids (40.401%) and dot matches indicate similar amino acids (64.470%).

FIG. 4 illustrated the predicted transmembrane domains for HGBER32 (SEQ ID NO:2).

DETAILED DESCRIPTION OF THE INVENTION

Figure 2A:
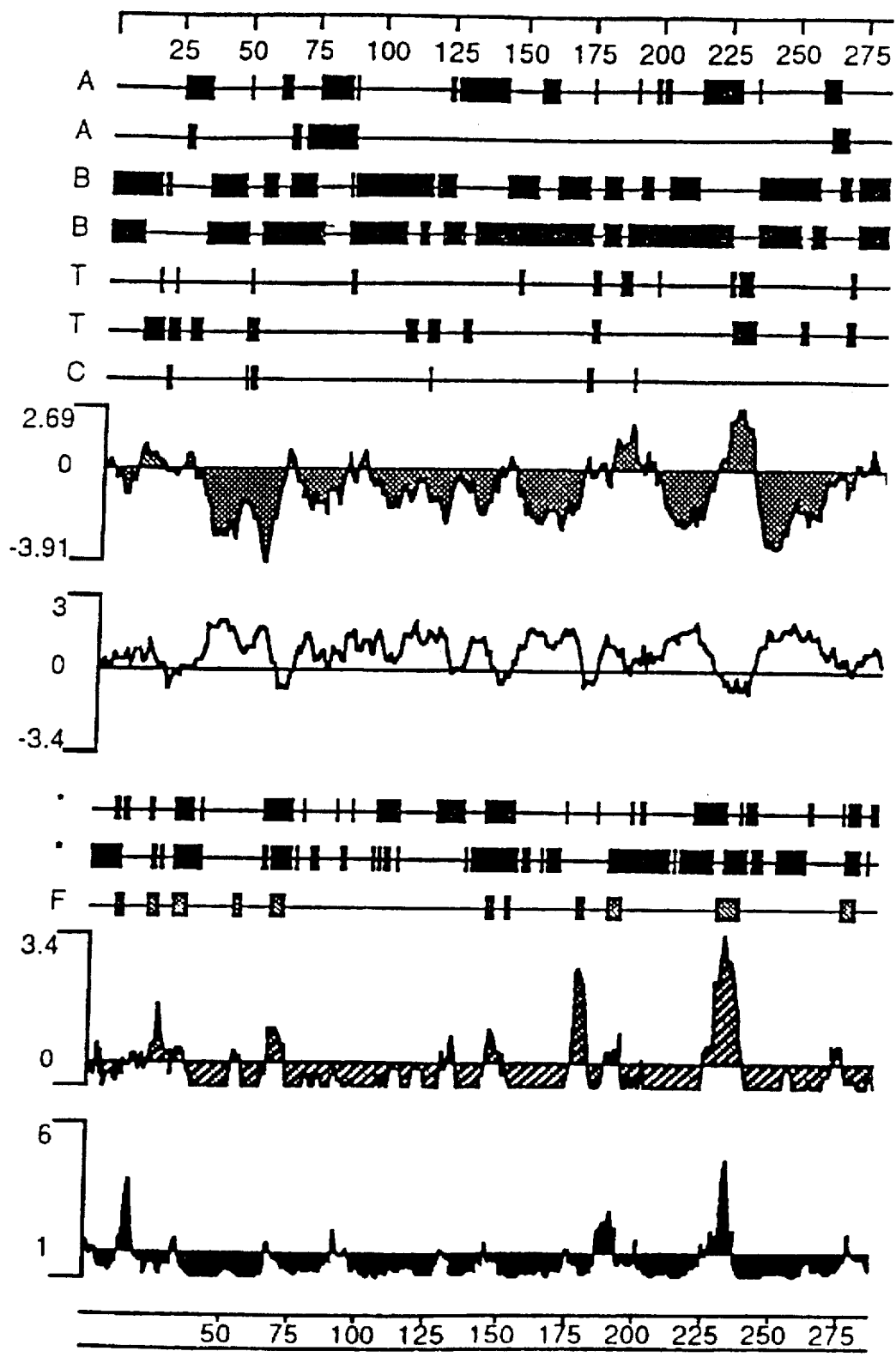
FIGS. 2A and 2B, collectively, are an illustration of the secondary structural features of the HGBER32 G-protein coupled receptor. The first 7 illustrations set forth the regions of the amino acid sequence which are alpha helices, beta sheets, turn regions or coiled regions. The boxed areas are the areas which correspond to the region indicated. The second set of figures illustrate areas of the amino acid sequence which are exposed to intracellular, cytoplasmic or are membrane-spanning. The hydrophilicity plot illustrates areas of the protein sequence which are the lipid bilayer of the membrane and are, therefore, hydrophobic, and areas outside the lipid bilayer membrane which are hydrophilic. The antigenic index corresponds to the hydrophilicity plot, since antigenic areas are areas outside the lipid bilayer membrane and are capable of binding antigens. The surface probability plot further corresponds to the antigenic index and the hydrophilicity plot. The amphipathic plots show those regions of the protein sequences which are polar and non-polar. The flexible regions corresond to the second set of illustrations in the sense that flexible regions are those which are outside the membrane and inflexible regions are transmembrane regions.
Figure 2B:
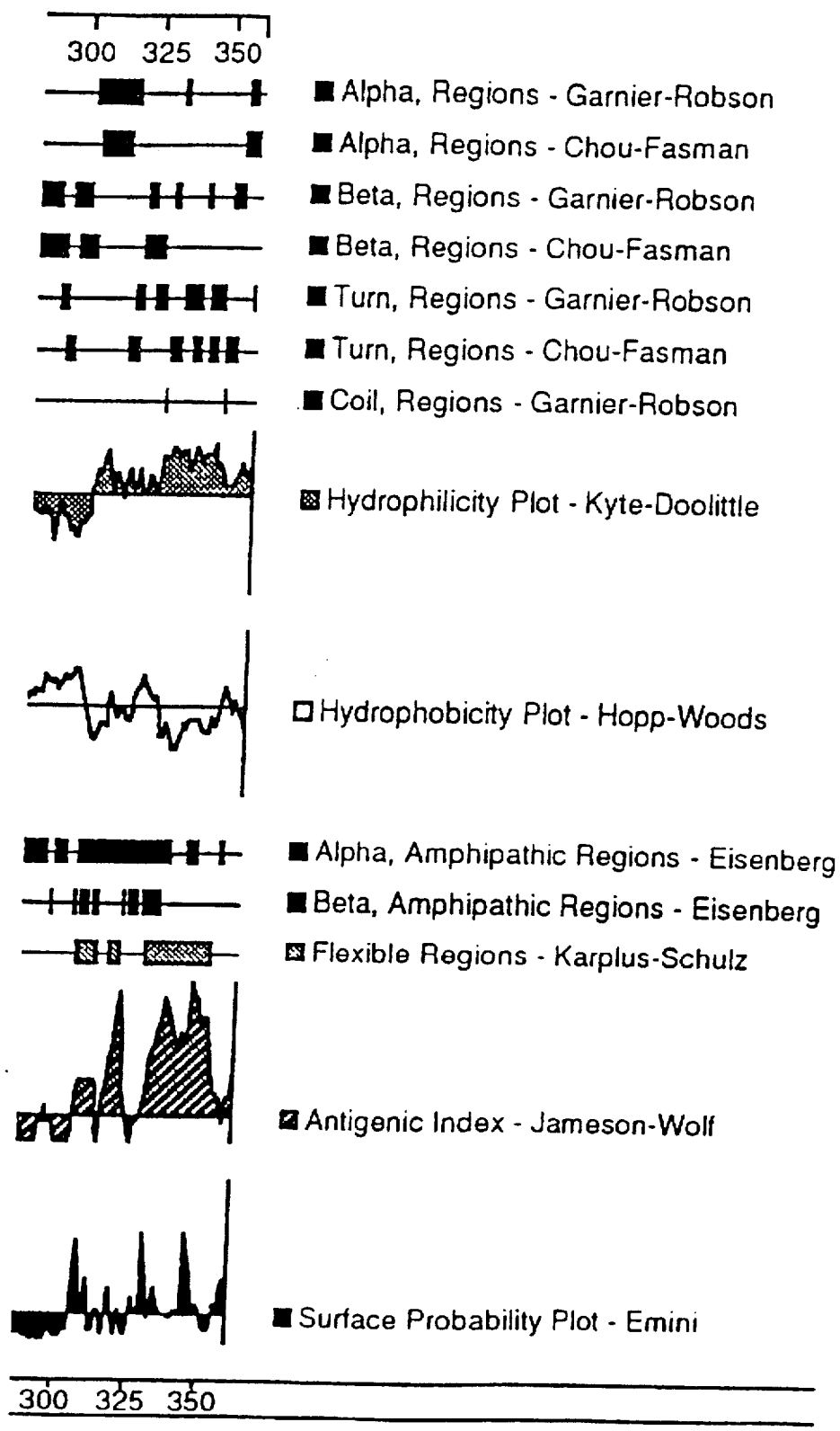

In accordance with an aspect of the present invention, there are provided isolated nucleic acids (polynucleotides) which encode for the mature polypeptide having the deduced amino acid sequence of FIGS. 1A, 1B, 1C and 1D, collectively, (SEQ ID NO:2) or for the mature polypeptide encoded by the cDNA of the clone deposited as ATCC Deposit No. 97187 on Jun. 1, 1995, with the ATCC, 12301 Parklawn Drive, Rockville, Md. 20852. Since the strain referred to as ATCC No 97187 is being maintained under the terms of the Budapest Treaty, it will be made available to a patent office signatory to the Budapest Treaty.

The polynucleotide of this invention was discovered in a cDNA library derived from human gall bladder tissue. It is structurally related to the G protein-coupled receptor family. It contains an open reading frame encoding a mature protein of 355 amino acid residues. The protein exhibits the highest degree of homology to human-monocyte chemoattractant protein 1 receptor (MCP-1b) with about 40% identity and about 64% similarity.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A, 1B, 1C and 1D, collectively (SEQ ID NO:1) or that of the deposited clone or may be a different coding sequence which coding sequence, as a result of the redundancy or degeneracy of the genetic code, encodes the same mature polypeptide as the DNA of FIGS. 1A, 1B, 1C, 1D, collectively (SEQ ID NO:1) or the deposited cDNA.

The polynucleotides which encode for the mature polypeptides of FIGS. 1A, 1B, 1C, and 1D, collectively, (SEQ ID NO:2) or for the mature polypeptide encoded by the deposited cDNA may include: only the coding sequence for the mature polypeptide; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A, 1B, 1C and 1D, collectively, (SEQ ID NO:2) or the polypeptide encoded by the cDNA of the deposited clone. The variants of the polynucleotides may be a naturally occurring allelic variant of the polynucleotides or a non-naturally occurring variant of the polynucleotides.

Thus, the present invention includes polynucleotides encoding the same mature polypeptide as shown in FIGS. 1A, 1B, 1C, and 1D, collectively, (SEQ ID NO:2) or the same mature polypeptide encoded by the cDNA of the deposited clone as well as variants of such polynucleotides which variants encode for a fragment, derivative or analog of the polypeptide of FIGS. 1A, 1B, 1C and 1D, collectively, (SEQ ID NO:2) or the polypeptide encoded by the cDNA of the deposited clone. Such nucleotide variants include deletion variants, substitution variants and addition or insertion variants.

As hereinabove indicated, the polynucleotides may have a coding sequence which is a naturally occurring allelic variant of the coding sequence shown in FIGS. 1A, 1B, 1C and 1D, collectively, (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptides.

The polynucleotides may also encode for a soluble form of the receptor polypeptide of the present invention which is the extracellular portion of the polypeptide which has been cleaved from the TM and intracellular domain of the full-length polypeptide of the present invention.

The polynucleotides of the present invention may also have the coding sequence fused in frame to a marker sequence which allows for purification of the polypeptides of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A, 1B, 1C and 1D, collectively (SEQ ID NO:1) or the deposited cDNA(s), i.e. function as a soluble receptor polypeptide by retaining the ability to bind the ligands for the receptor even though the polypeptide does not function as a membrane bound receptor polypeptide, for example, by eliciting a second messenger response.

Alternatively, the polynucleotide may have at least 20 bases, preferably at least 30 bases, and more preferably at least 50 bases which hybridize to a polynucleotide of the present invention and which has an identity thereto, as hereinabove described. Such polynucleotides may be employed as probes for the polynucleotide of SEQ ID NO:1, for example, for recovery of the polynucleotide or as a diagnostic probe or as a PCR primer.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a G-protein coupled receptor polypeptide which has the deduced amino acid sequence of FIGS. 1A, 1B, 1C and 1D, collectively, (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIGS. 1A, 1B, 1C and 1D, collectively, (SEQ ID NO:2) or that encoded by the deposited cDNA, means a polypeptide which either retains substantially the same biological function or activity as such polypeptide, i.e. functions as a G-protein coupled receptor, or retains the ability to bind the ligand or the receptor even though the polypeptide does not function as a G-protein coupled receptor, for example, a soluble form of the receptor. An analog includes a proprotein which can be activated by cleavage of the proprotein portion to produce an active mature polypeptide.

The polypeptides of the present invention may be recombinant polypeptides, a natural polypeptides or synthetic polypeptides, preferably recombinant polypeptides.

The fragment, derivative or analog of the polypeptide of FIGS. 1A, 1B, 1C and 1D, collectively, (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide which is employed for purification of the mature polypeptide or (v) one in which a fragment of the polypeptide is soluble, i.e. not membrane bound, yet still binds ligands to the membrane bound receptor. Such fragments, derivatives and analogs are deemed to be within the scope of those skilled in the art from the teachings herein.

The polypeptides and polynucleotides of the present invention are preferably provided in an isolated form, and preferably are purified to homogeneity.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The term "gene" means the segment of DNA involved in producing a polypeptide chain; it includes regions preceding and following the coding region "leader and trailer" as well as intervening sequences (introns) between individual coding segments (exons).

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the G-protein coupled receptor genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.\ coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.\ coli.$ The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E.\ coli$, Streptomyces, *Salmonella typhimurium*; fungal cells, such as yeast; insect cells such as *Drosophila S2* and *Spodoptera Sf9*; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); pTRC99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Fragments of the polypeptides of the present invention may be employed for producing the corresponding full-length polypeptide by peptide synthesis, therefore, the fragments may be employed as intermediates for producing the full-length polypeptides. Fragments of the polynucleotides of the present invention may be used in a similar manner to synthesize the full-length polynucleotides of the present invention.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The G-protein coupled receptor polypeptide of the present invention can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

Fragments of the full length G-protein coupled receptor genes may be employed as a hybridization probe for a cDNA library to isolate the full length genes and to isolate other genes which have a high sequence similarity to the gene or similar biological activity. Probes of this type have at least 20 bases, preferably 30 bases and most preferably 50 bases or more. The probe may also be used to identify a cDNA clone corresponding to a full length transcript and a genomic clone or clones that contain the complete G-protein coupled receptor gene including regulatory and promotor regions, exons, and introns. As an example of a screen comprises isolating the coding region of the G-protein coupled receptor gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The G-protein coupled receptors of the present invention may be employed in a process for screening for compounds which activate (agonists) or inhibit activation (antagonists) of the receptor polypeptide of the present invention.

In general, such screening procedures involve providing appropriate cells which express the receptor polypeptide of the present invention on the surface thereof. Such cells include cells from mammals, yeast, drosophila or E. Coli. In particular, a polynucleotide encoding the receptor of the present invention is employed to transfect cells to thereby express the G-protein coupled receptor. The expressed receptor is then contacted with a test compound to observe binding, stimulation or inhibition of a functional response.

One such screening procedure involves the use of melanophores which are transfected to express the G-protein coupled receptor of the present invention. Such a screening technique is described in PCT WO 92/01810 published Feb. 6, 1992.

Thus, for example, such assay may be employed for screening for a compound which inhibits activation of the receptor polypeptide of the present invention by contacting the melanophore cells which encode the receptor with both the receptor ligand and a compound to be screened. Inhibition of the signal generated by the ligand indicates that a compound is a potential antagonist for the receptor, i.e., inhibits activation of the receptor.

The screen may be employed for determining a compound which activates the receptor by contacting such cells with compounds to be screened and determining whether such compound generates a signal, i.e., activates the receptor.

Other screening techniques include the use of cells which express the G-protein coupled receptor (for example, transfected CHO cells) in a system which measures extracellular pH changes caused by receptor activation, for example, as described in Science, volume 246, pages 181–296 (October 1989). For example, compounds may be contacted with a cell which expresses the receptor polypeptide of the present invention and a second messenger response, e.g. signal transduction or pH changes, may be measured to determine whether the potential compound activates or inhibits the receptor.

Another such screening technique involves introducing RNA encoding the G-protein coupled receptor into Xenopus oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another screening technique involves expressing the G-protein coupled receptor in which the receptor is linked to a phospholipase C or D. As representative examples of such cells, there may be mentioned endothelial cells, smooth muscle cells, embryonic kidney cells, etc. The screening may be accomplished as hereinabove described by detecting activation of the receptor or inhibition of activation of the receptor from the phospholipase second signal.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the G-protein coupled receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

G-protein coupled receptors are ubiquitous in the mammalian host and are responsible for many biological functions, including many pathologies. Accordingly, it is desirous to find compounds and drugs which stimulate the G-protein coupled receptor on the one hand and which can inhibit the function of a G-protein coupled receptor on the other hand.

For example, compounds which activate the G-protein coupled receptor may be employed for therapeutic purposes, such as the treatment of asthma, Parkinson's disease, acute heart failure, hypotension, urinary retention, and osteoporosis.

In general, compounds which inhibit activation of the G-protein coupled receptor may be employed for a variety of therapeutic purposes, for example, for the treatment of hypertension, angina pectoris, myocardial infarction, ulcers, asthma, allergies, benign prostatic hypertrophy and psychotic and neurological disorders, including schizophrenia, manic excitement, depression, delirium, dementia or severe mental retardation, dyskinesias, such as Huntington's disease or Gilles dila Tourett's syndrome, among others. Compounds which inhibit G-protein coupled receptors have also been useful in reversing endogenous anorexia and in the control of bulimia.

An antibody may antagonize a G-protein coupled receptor of the present invention, or in some cases an oligopeptide, which bind to the G-protein coupled receptor but does not elicit a second messenger response such that the activity of the G-protein coupled receptors is prevented. Antibodies include anti-idiotypic antibodies which recognize unique determinants generally associated with the antigen-binding site of an antibody. Potential antagonist compounds also include proteins which are closely related to the ligand of the G-protein coupled receptors, i.e. a fragment of the ligand, which have lost biological function and when binding to the G-protein coupled receptor, elicit no response.

An antisense construct prepared through the use of antisense technology, may be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of G-protein coupled receptor. The antisense RNA oligonucleotide hybridizes to the mRNA in vivo and blocks translation of mRNA molecules into G-protein coupled receptor (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of G-protein coupled receptor.

A small molecule which binds to the G-protein coupled receptor, making it inaccessible to ligands such that normal biological activity is prevented, for example small peptides or peptide-like molecules, may also be used to inhibit activation of the receptor polypeptide of the present invention.

A soluble form of the G-protein coupled receptor, e.g. a fragment of the receptors, may be used to inhibit activation of the receptor by binding to the ligand to a polypeptide of the present invention and preventing the ligand from interacting with membrane bound G-protein coupled receptors.

This invention additionally provides a method of treating an abnormal condition related to an excess of G-protein coupled receptor activity which comprises administering to a subject the inhibitor compounds as hereinabove described along with a pharmaceutically acceptable carrier in an amount effective to inhibit activation by blocking binding of ligands to the G-protein coupled receptors, or by inhibiting a second signal, and thereby alleviating the abnormal conditions.

The invention also provides a method of treating abnormal conditions related to an under-expression of G-protein coupled receptor activity which comprises administering to a subject a therapeutically effective amount of a compound which activates the receptor polypeptide of the present invention as described above in combination with a pharmaceutically acceptable carrier, to thereby alleviate the abnormal conditions.

The soluble form of the G-protein coupled receptor, and compounds which activate or inhibit such receptor, may be employed in combination with a suitable pharmaceutical carrier. Such compositions comprise a therapeutically effective amount of the polypeptide or compound, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, the pharmaceutical compositions will be administered in an amount of at least about 10 μg/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

The G-protein coupled receptor polypeptides, and compounds which activate or inhibit which are also compounds may be employed in accordance with the present invention by expression of such polypeptides in vivo, which is often referred to as "gene therapy."Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., Biotechniques, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the genes encoding the polypeptides.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pg. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The present invention also provides a method for determining whether a ligand not known to be capable of binding to a G-protein coupled receptor of the present invention can bind to such receptor which comprises contacting a mammalian cell which expresses a G-protein coupled receptor with the ligand under conditions permitting binding of ligands to the G-protein coupled receptor, detecting the presence of a ligand which binds to the receptor and thereby determining whether the ligand binds to the G-protein coupled receptor.

This invention further provides a method of screening drugs to identify drugs which specifically interact with, and bind to, the human G-protein coupled receptors on the surface of a cell which comprises contacting a mammalian cell comprising an isolated DNA molecule encoding the G-protein coupled receptor with a plurality of drugs, determining those drugs which bind to the mammalian cell, and thereby identifying drugs which specifically interact with and bind to a human G-protein coupled receptor of the present invention. Such drugs may then be used therapeutically to either activate or inhibit activation of the receptors of the present invention.

This invention also provides a method of detecting expression of the G-protein coupled receptor on the surface of a cell by detecting the presence of mRNA coding for a G-protein coupled receptor which comprises obtaining total mRNA from the cell and contacting the mRNA so obtained with a nucleic acid probe of the present invention capable of specifically hybridizing with a sequence included within the sequence of a nucleic acid molecule encoding a human G-protein coupled receptor under hybridizing conditions, detecting the presence of mRNA hybridized to the probe, and thereby detecting the expression of the G-protein coupled receptor by the cell.

This invention is also related to the use of the G-protein coupled receptor genes as part of a diagnostic assay for detecting diseases or susceptibility to diseases related to the presence of mutations in the nucleic acid sequences with encode the receptor polypeptides of the present invention. Such diseases, by way of example, are related to cell transformation, such as tumors and cancers.

Individuals carrying mutations in the human G-protein coupled receptor gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding the G-protein coupled receptor proteins can be used to identify and analyze G-protein coupled receptor mutations. For example, deletions and insertions can be detected by a change in size of the amplified product in comparison to the normal genotype. Point mutations can be identified by hybridizing amplified DNA to radiolabeled G-protein coupled receptor RNA or alternatively, radiolabeled G-protein coupled receptor antisense DNA sequences. Perfectly matched sequences can be distinguished from mismatched duplexes by RNase A digestion or by differences in melting temperatures.

Sequence differences between the reference gene and gene having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of soluble forms of the receptor polypeptides of the present invention in various tissues. Assays used to detect levels of the soluble receptor polypeptides in a sample derived from a host are well known to those of skill in the art and include radioimmunoassays, competitive-binding assays, Western blot analysis and preferably as ELISA assay.

An ELISA assay initially comprises preparing an antibody specific to antigens of the receptor polypeptide, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any receptor polypeptides of the present invention attached to the polystyrene dish. All unbound monoclonal antibody is washed out with buffer. The reporter antibody linked to horseradish peroxidase is now placed in the dish resulting in binding of the reporter antibody to any monoclonal antibody bound to receptor proteins. Unattached reporter antibody is then washed out. Peroxidase substrates are then added to the dish and the amount of color developed in a given time period is a measurement of the amount of receptor proteins present in a given volume of patient sample when compared against a standard curve.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with gene associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: A Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described here are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Expression of Recombinant HGBER32 in COS 7 Cells

The expression of plasmid, HGBER32 HA is derived from a vector pcDNA3 (Invitrogen) containing: 1) SV40 origin of replication, 2) ampicillin resistance gene, 3) E. coli replication origin, 4) CMV promoter followed by a polylinker region, a SV40 intron and polyadenylation site. A DNA fragment encoding the entire HGBER32 precursor and a HA tag fused in frame to its 3' end was cloned into the polylinker region of the vector, therefore, the recombinant protein expression is directed by the CMV promoter. The HA tag corresponds to an epitope derived from the influenza hemagglutinin protein as previously described (Wilson et al., Cell, 37:767, 1984). The infusion of HA tag to the target protein allows easy detection of the recombinant protein with an antibody that recognizes the HA epitope.

The plasmid construction strategy is described as follows:

The DNA sequence encoding HGBER32, ATCC #97187, was constructed by PCR on a genomic lambda clone using two primers: the 5' primer; 5'ACCA GGATCCGCTGCCTTGATGGATTAT (SEQ ID NO:4) contains a BAMHI site followed by 9 nucleotides of HGBER32 coding sequence starting from the initiation codon; the 3' primer (SEQ ID NO:5) 5'CTGCT TCTAGAATGCCATTCAAGAAAATGTT contains complementary sequences to XbaI site, translation stop codon, 10 nucleotides of the HGBER32 coding sequence (not including the stop codon). Therefore, the PCR product contains a BAMHI site, HGBER32 coding sequence followed by a translation termination stop codon and an XbaI site. The PCR amplified DNA fragment and the vector, pcDNAI/Amp, were digested with BAMHI and XbaI restriction enzyme and ligated. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant HGBER32, COS 7 cells were transfected with the expression vector by DEAE-DEXTRAN method (Sambrook et al., Molecular Cloning: A Laboratory Manual, Second Edition, Cold Spring Laboratory Press, 1989). The expression of the HGBER32 HA protein was detected by radiolabelling and immunoprecipitation method (Harlow and Lane, Antibodies: A Laboratory Manual, Cold Spring Harbor Laboratory Press, 1988). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5) (Wilson et al., Id., 37:767, 1984). Both cell lysate and culture media were precipitated with a HA specific monoclonal antibody. Proteins precipitated were analyzed on 15% SDS-PAGE gels.

EXAMPLE 2

Cloning and Expression of HGBER32 Using the Baculovirus Expression System

The DNA sequence encoding the full length HGBER32 protein, ATCC #97187, was amplified using PCR oligonucleotide primers corresponding to the 5' and 3' sequences of the gene:

The 5' primer has the sequence GTGACCGGATC-CCGCTGCCTTGCCGCCAT CATGGATTATACACTTGACCTCAGTG (SEQ ID NO:6) and contains a BAMHI restriction enzyme site (in bold) followed by 18 nucleotides resembling an efficient signal for the initiation of translation in eukaryotic cells (Kozak, J. Mol. Biol., 196:947–950, 1987), and just behind the first 25 nucleotides of the HGBER32 gene (the initiation codon for translation "ATG" is underlined).

The 3' primer has the sequence TTAATCTAGAGTCT-TCATTGATCCTCCCAAATG (SEQ ID NO:7) and contains the cleavage site for the restriction endonuclease XbaI and 4 nucleotides complementary to the 3' non-translated sequence of the HGBER32 gene. The amplified sequences were isolated from a 1% agarose gel using a commercially available kit ("Geneclean," BIO 101 Inc., La Jolla, Calif.). The fragment was then digested with the endonucleases BAMHI and XbaI and then purified as described in Example 1. This fragment is designated F2.

The vector pA2 (modification of PUL941 vector, discussed below) is used for the expression of the HGBER32 protein using the baculovirus expression system (for review see: Summers and Smith, *A Manual of Methods for Baculovirus Vectors and Insect Cell Culture Procedures*, Texas Agricultural Experimental Station Bulletin No. 1555, 1987). This expression vector contains the strong polyhedrin promoter of the Autographa californica nuclear polyhedrosis virus (AcMNPV) followed by the recognition sites for the restriction endonucleases BAMHI and XbaI. The polyadenylation site of the simian virus (SV)40 is used for efficient polyadenylation. For an easy selection of recombinant viruses the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pA2 such as pRG1, pAc373, pVL941 and pAcIM1 (Luckow and Summers, *Virology*, 170:31–39).

The plasmid was digested with the restriction enzymes BAMHI and XbaI and then dephosphorylated using calf intestinal phosphatase by procedures known in the art. The DNA was then isolated from a 1% agarose gel as described in Example 1. This vector DNA is designated V2.

Fragment F2 and the dephosphorylated plasmid V2 were ligated with T4 DNA ligase. *E. coli* HB101 cells were then transformed and bacteria identified that contained the plasmid (pBac-HGBER32) with the HGBER32 gene. The sequence of the cloned fragment was confirmed by DNA sequencing.

5 µg of the plasmid pBac-HGPCR were co-transfected with 1.0 µg of a commercially available linearized baculovirus ("BaculoGold™ baculovirus DNA", Pharmingen, San Diego, Calif.) using the lipofection method (Felgner et al., *Proc. Natl. Acad. Sci. USA*, 84:7413–7417 (1987)).

1 µg of BaculoGold™ virus DNA and 5 µg of the plasmid pBac-HGBER32 were mixed in a sterile well of a microtiter plate containing 50 µl of serum free Grace's medium (Life Technologies Inc., Gaithersburg, Md.). Afterwards 10 µl Lipofectin plus 90 µl Grace's medium were added, mixed and incubated for 15 minutes at room temperature. Then the transfection mixture was added drop wise to the Sf9 insect cells (ATCC CRL 1711) seeded in a 35 mm tissue culture plate with 1 ml Grace' medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay was performed in a manner similar to that described by Summers and Smith, supra. As a modification, an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses were added to the cells and blue stained plaques were picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-HGBER32 at a multiplicity of infection (MOI) of 2. Six hours later the medium was removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) were added. The cells were further incubated for 16 hours before they were harvested by centrifugation and the labelled proteins were visualized by SDS-PAGE and autoradiography.

EXAMPLE 3

Expression Pattern of HGBER32 in Human Tissue

Northern blot analysis is carried out to examine the levels of expression of HGBER32 in human tissues. Total cellular RNA samples are isolated with RNAzol™ B system (Biotecx Laboratories, Inc. 6023 South Loop East, Houston, Tex. 77033). About 10 µg of total RNA isolated from each human tissue specified is separated on 1% agarose gel and blotted onto a nylon filter. (Sambrook et al., supra. The labeling reaction is done according to the Stratagene Prime-It kit with 50 ng DNA fragment. The labeled DNA is purified with a Select-G-50 column. (5 Prime–3 Prime, Inc. 5603 Arapahoe Road, Boulder, Colo. 80303). The filter is then hybridized with radioactive labeled full length HGBER32 gene at 1,000,000 cpm/ml in 0.5M NaPO$_4$, pH 7.4 and 7% SDS overnight at 65° C. After being washed twice at room temperature and twice at 60° C. with 0.5×SSC, 0.1% SDS, the filter is then exposed at −70° C. overnight with an intensifying screen. The messenger RNA for HGBER32 is abundant in human cerebellum tissue.

EXAMPLE 4

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al. DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer having contains a HindIII site. Equal quantities of the Moloney murine sarcoma virus linear backbone and the EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention were possible in light of the above teachings and, therefore, within the scope of the appended claims, the invention may be practiced otherwise than as particularly described.

What is claimed is:

1. An isolated polynucleotide comprising a polynucleotide coding sequence having at least 95% identity to a member selected from the group consisting of:

(a) a polynucleotide sequence encoding a polypeptide comprising amino acids 2 to 355 of SEQ ID NO:2; and (b) the complement of (a), providing that when said isolated polynucleotide comprises a polynucleotide sequence encoding amino acids 2 to 355 of SEQ ID NO:2, said isolated polynucleotide is separated from one or more of its neighboring genes from the same chromosome gene.

2. The isolated polynucleotide of claim 1 wherein said member is (a).

3. The isolated polynucleotide of claim 1 wherein said member is (a) and the polypeptide comprises amino acids 1 to 355 of SEQ ID No:2.

4. The isolated polynucleotide of claim 1 comprising a polynucleotide sequence encoding a polypeptide comprising the amino acid sequence identical to amino acids 2 to 355 of SEQ ID NO:2.

5. The isolated polynucleotide of claim 1, wherein the isolated polynucleotide is DNA.

6. The isolated polynucleotide of claim 1 comprising a polynucleotide sequence encoding a polypeptide comprising the amino sequence identical to amino acids 1 to 355 of SEQ ID NO:2.

7. The isolated polynucleotide of claim 1, wherein said isolated polynucleotide is RNA.

8. A method of making a recombinant vector comprising inserting the isolated polynucleotide of claim 2 into a vector, wherein said polynucleotide is DNA.

9. A recombinant vector comprising the isolated polynucleotide of claim 2, wherein said isolated polynucleotide is DNA.

10. A recombinant host cell comprising the isolated polynucleotide of claim 2, wherein said isolated polynucleotide is DNA.

11. A method for producing a polypeptide comprising expressing from the recombinant cell of claim 10 the polypeptide encoded by said isolated polynucleotide.

12. A process for producing a polypeptide comprising:
expressing from a recombinant cell containing the isolated polynucleotide of claim 4 the polypeptide encoded by said isolated polynucleotide.

13. A process for producing a polypeptide comprising:
expressing from a recombinant cell containing the (isolated) polynucleotide of claim 6 the polypeptide encoded by said isolated polynucleotide.

14. The isolated polynucleotide of claim 1 comprising nucleotides 434 to 1495 of SEQ ID NO:1.

15. The isolated polynucleotide of claim 1 comprising nucleotides 431 to 1495 of SEQ ID NO:1.

16. The isolated polynucleotide of claim 1 comprising the nucleotides of the sequence of SEQ ID NO:1.

17. An isolated polynucleotide comprising a polynucleotide sequence having at least 95% identity to the polynucleotide sequence of a member selected from the group consisting of:

(a) a polynucleotide sequence encoding the same mature polypeptide encoded by the human cDNA in ATCC Deposit No. 97187; and (b) the complement of (a).

18. The isolated polynucleotide of claim 17, wherein the member is (a).

19. The isolated polynucleotide of claim 17, wherein the polynucleotide sequence of said polynucleotide comprises DNA identical to the coding portion of the human cDNA in ATCC Deposit No. 97187 which encodes a mature polypeptide.

20. A recombinant vector comprising the isolated polynucleotide of claim 17, wherein said isolated polynucleotide is DNA.

21. A process for producing a polypeptide comprising:
expressing from a recombinant cell containing the isolated polynucleotide of claim 15 the polypeptide encoded by said polynucleotide.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 1586 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 431..1495

( x i ) SEQUENCE DESCRIPTION: SEQ ID NO:1:

```
CCTCTTTGGG  GTCCAAGTGA  ATCCTTCTGC  CTCAGCCTCC  TGAGTAGCTA  GGATTACAGG      60

CATGCACCCG  CCATGCCCGG  CTAATTTTTG  TAATTTTTAG  TAGAGACGGG  GTTTCCCCAT     120

GTTGCCAAGG  CTGGTCTTGA  ACCCCTGACC  TCAGGTGATC  TGCCTCACCT  TGGCCTCCCA     180

AAGTGCTAGG  ATTACAGGCA  TGAGCCACAG  CTCCCGGTCT  ATCATTTAAC  CTTAATTACA     240

TCTTTAAAGG  CCCAAATAGT  CTCACCCACT  CCAAATAGTC  ACACCCACAC  CGGAGGTTGA     300

GCACTTCAAC  ACATGAATTT  GGGGAGGACA  CAGTTCAGTC  CATAACATCC  CCCTAATTTT     360

TAAAAAATAA  AAATGTTTTT  AAGGAGTGAA  TGTCTTTTAT  GTGTCTCTGT  GACCAGGTCC     420
```

```
CGCTGCCTTG  ATG  GAT  TAT  ACA  CTT  GAC  CTC  AGT  GTG  ACA  ACA  GTG  ACC      469
            Met  Asp  Tyr  Thr  Leu  Asp  Leu  Ser  Val  Thr  Thr  Val  Thr
              1              5                            10

GAC  TAC  TAC  TAC  CCT  GAT  ATC  TTC  TCA  AGC  CCC  TGT  GAT  GCG  GAA  CTT     517
Asp  Tyr  Tyr  Tyr  Pro  Asp  Ile  Phe  Ser  Ser  Pro  Cys  Asp  Ala  Glu  Leu
          15                      20                      25

ATT  CAG  ACA  AAT  GGC  AAG  TTG  CTC  CTT  GCT  GTC  TTT  TAT  TGC  CTC  CTG     565
Ile  Gln  Thr  Asn  Gly  Lys  Leu  Leu  Leu  Ala  Val  Phe  Tyr  Cys  Leu  Leu
     30                  35                      40                      45

TTT  GTA  TTC  AGT  CTT  CTG  GGA  AAC  AGC  CTG  GTC  ATC  CTG  GTC  CTT  GTG     613
Phe  Val  Phe  Ser  Leu  Leu  Gly  Asn  Ser  Leu  Val  Ile  Leu  Val  Leu  Val
                     50                       55                     60

GTC  TGC  AAG  AAG  CTG  AGG  AGC  ATC  ACA  GAT  GTA  TAC  CTC  TTG  AAC  CTG     661
Val  Cys  Lys  Lys  Leu  Arg  Ser  Ile  Thr  Asp  Val  Tyr  Leu  Leu  Asn  Leu
             65                      70                      75
```

| | | | | | | | | | | | | | | | | |
|---|---|---|---|---|---|---|---|---|---|---|---|---|---|---|---|---|
| GCC | CTG | TCT | GAC | CTG | CTT | TTT | GTC | TTC | TCC | TTC | CCC | TTT | CAG | ACC | TAC | 709 |
| Ala | Leu | Ser 80 | Asp | Leu | Leu | Phe | Val 85 | Phe | Ser | Phe | Pro | Phe 90 | Gln | Thr | Tyr | |
| TAT | CTG | CTG | GAC | CAG | TGG | GTG | TTT | GGG | ACT | GTA | ATG | TGC | AAA | GTG | GTG | 757 |
| Tyr | Leu 95 | Leu | Asp | Gln | Trp 100 | Val | Phe | Gly | Thr | Val 105 | Met | Cys | Lys | Val | Val | |
| TCT | GGC | TTT | TAT | TAC | ATT | GGC | TTC | TAC | AGC | AGC | ATG | TTT | TTC | ATC | ACC | 805 |
| Ser 110 | Gly | Phe | Tyr | Tyr 115 | Ile | Gly | Phe | Tyr | Ser | Ser 120 | Met | Phe | Phe | Ile | Thr 125 | |
| CTC | ATG | AGT | GTG | GAC | AGG | TAC | CTG | GCT | GTT | GTC | CAT | GCC | GTG | TAT | GCC | 853 |
| Leu | Met | Ser | Val | Asp 130 | Arg | Tyr | Leu | Ala | Val 135 | Val | His | Ala | Val | Tyr 140 | Ala | |
| CTA | AAG | GTG | AGG | ACG | ATC | AGG | ATG | GGC | ACA | ACG | CTG | TGC | CTG | GCA | GTA | 901 |
| Leu | Lys | Val | Arg 145 | Thr | Ile | Arg | Met | Gly 150 | Thr | Thr | Leu | Cys | Leu 155 | Ala | Val | |
| TGG | CTA | ACC | GCC | ATT | ATG | GCT | ACC | ATC | CCA | TTG | CTA | GTG | TTT | TAC | CAA | 949 |
| Trp | Leu | Thr 160 | Ala | Ile | Met | Ala | Thr 165 | Ile | Pro | Leu | Leu | Val 170 | Phe | Tyr | Gln | |
| GTG | GCC | TCT | GAA | GAT | GGT | GTT | CTA | CAG | TGT | TAT | TCA | TTT | TAC | AAT | CAA | 997 |
| Val | Ala 175 | Ser | Glu | Asp | Gly | Val 180 | Leu | Gln | Cys | Tyr | Ser 185 | Phe | Tyr | Asn | Gln | |
| CAG | ACT | TTG | AAG | TGG | AAG | ATC | TTC | ACC | AAC | TTC | AAA | ATG | AAC | ATT | TTA | 1045 |
| Gln 190 | Thr | Leu | Lys | Trp | Lys 195 | Ile | Phe | Thr | Asn | Phe 200 | Lys | Met | Asn | Ile | Leu 205 | |
| GGC | TTG | TTG | ATC | CCA | TTC | ACC | ATC | TTT | ATG | TTC | TGC | TAC | ATT | AAA | ATC | 1093 |
| Gly | Leu | Leu | Ile | Pro 210 | Phe | Thr | Ile | Phe | Met 215 | Phe | Cys | Tyr | Ile | Lys 220 | Ile | |
| CTG | CAC | CAG | CTG | AAG | AGG | TGT | CAA | AAC | CAC | AAC | AAG | ACC | AAG | GCC | ATC | 1141 |
| Leu | His | Gln | Leu 225 | Lys | Arg | Cys | Gln | Asn 230 | His | Asn | Lys | Thr | Lys 235 | Ala | Ile | |
| AGG | TTG | GTG | CTC | ATT | GTG | GTC | ATT | GCA | TCT | TTA | CTT | TTC | TGG | GTC | CCA | 1189 |
| Arg | Leu | Val 240 | Leu | Ile | Val | Val | Ile 245 | Ala | Ser | Leu | Leu | Phe 250 | Trp | Val | Pro | |
| TTC | AAC | GTG | GTT | CTT | TTC | CTC | ACT | TCC | TTG | CAC | AGT | ATG | CAC | ATC | TTG | 1237 |
| Phe | Asn 255 | Val | Val | Leu | Phe | Leu 260 | Thr | Ser | Leu | His | Ser 265 | Met | His | Ile | Leu | |
| GAT | GGA | TGT | AGC | ATA | AGC | CAA | CAG | CTG | ACT | TAT | GCC | ACC | CAT | GTC | ACA | 1285 |
| Asp 270 | Gly | Cys | Ser | Ile | Ser 275 | Gln | Gln | Leu | Thr | Tyr 280 | Ala | Thr | His | Val | Thr 285 | |
| GAA | ATC | ATT | TCC | TTT | ACT | CAC | TGC | TGT | GTG | AAC | CCT | GTT | ATC | TAT | GCT | 1333 |
| Glu | Ile | Ile | Ser | Phe 290 | Thr | His | Cys | Cys | Val 295 | Asn | Pro | Val | Ile | Tyr 300 | Ala | |
| TTT | GTT | GGG | GAG | AAG | TTC | AAG | AAA | CAC | CTC | TCA | GAA | ATA | TTT | CAG | AAA | 1381 |
| Phe | Val | Gly | Glu 305 | Lys | Phe | Lys | Lys | His 310 | Leu | Ser | Glu | Ile | Phe 315 | Gln | Lys | |
| AGT | TGC | AGC | CAA | ATC | TTC | AAC | TAC | CTA | GGA | AGA | CAA | ATG | CCT | AGG | GAG | 1429 |
| Ser | Cys | Ser 320 | Gln | Ile | Phe | Asn | Tyr 325 | Leu | Gly | Arg | Gln | Met 330 | Pro | Arg | Glu | |
| AGC | TGT | GAA | AAG | TCA | TCA | TCC | TGC | CAG | CAG | CAC | TCC | TCC | CGT | TCC | TCC | 1477 |
| Ser | Cys 335 | Glu | Lys | Ser | Ser | Ser 340 | Cys | Gln | Gln | His | Ser 345 | Ser | Arg | Ser | Ser | |
| AGC | GTA | GAC | TAC | ATT | TTG | TAGGATCAAT | GAAGACTAAA | TATTAAAAAC | | | | | | | | 1525 |
| Ser 350 | Val | Asp | Tyr | Ile | Leu 355 | | | | | | | | | | | |

ATTTNCTTGA ATGGNATGCT AGTAGCAGNG GAGCAAAGGT GTGGGTGTGA AAGGTTTCCA 1585

A 1586

( 2 ) INFORMATION FOR SEQ ID NO:2:

(i) SEQUENCE CHARACTERISTICS:
  (A) LENGTH: 355 amino acids
  (B) TYPE: amino acid
  (D) TOPOLOGY: linear (ii) MOLECULE TYPE: protein (xi) SEQUENCE DESCRIPTION: SEQ ID NO:2:

```
Met Asp Tyr Thr Leu Asp Leu Ser Val Thr Val Thr Asp Tyr Tyr
 1               5                  10                  15

Tyr Pro Asp Ile Phe Ser Ser Pro Cys Asp Ala Glu Leu Ile Gln Thr
                20                  25                  30

Asn Gly Lys Leu Leu Leu Ala Val Phe Tyr Cys Leu Leu Phe Val Phe
            35                  40                  45

Ser Leu Leu Gly Asn Ser Leu Val Ile Leu Val Leu Val Val Cys Lys
    50                  55                  60

Lys Leu Arg Ser Ile Thr Asp Val Tyr Leu Leu Asn Leu Ala Leu Ser
 65                  70                  75                  80

Asp Leu Leu Phe Val Phe Ser Phe Pro Phe Gln Thr Tyr Tyr Leu Leu
                85                  90                  95

Asp Gln Trp Val Phe Gly Thr Val Met Cys Lys Val Val Ser Gly Phe
            100                 105                 110

Tyr Tyr Ile Gly Phe Tyr Ser Ser Met Phe Phe Ile Thr Leu Met Ser
        115                 120                 125

Val Asp Arg Tyr Leu Ala Val Val His Ala Val Tyr Ala Leu Lys Val
    130                 135                 140

Arg Thr Ile Arg Met Gly Thr Thr Leu Cys Leu Ala Val Trp Leu Thr
145                 150                 155                 160

Ala Ile Met Ala Thr Ile Pro Leu Leu Val Phe Tyr Gln Val Ala Ser
                165                 170                 175

Glu Asp Gly Val Leu Gln Cys Tyr Ser Phe Tyr Asn Gln Gln Thr Leu
            180                 185                 190

Lys Trp Lys Ile Phe Thr Asn Phe Lys Met Asn Ile Leu Gly Leu Leu
        195                 200                 205

Ile Pro Phe Thr Ile Phe Met Phe Cys Tyr Ile Lys Ile Leu His Gln
    210                 215                 220

Leu Lys Arg Cys Gln Asn His Asn Lys Thr Lys Ala Ile Arg Leu Val
225                 230                 235                 240

Leu Ile Val Val Ile Ala Ser Leu Leu Phe Trp Val Pro Phe Asn Val
                245                 250                 255

Val Leu Phe Leu Thr Ser Leu His Ser Met His Ile Leu Asp Gly Cys
            260                 265                 270

Ser Ile Ser Gln Gln Leu Thr Tyr Ala Thr His Val Thr Glu Ile Ile
        275                 280                 285

Ser Phe Thr His Cys Cys Val Asn Pro Val Ile Tyr Ala Phe Val Gly
    290                 295                 300

Glu Lys Phe Lys Lys His Leu Ser Glu Ile Phe Gln Lys Ser Cys Ser
305                 310                 315                 320

Gln Ile Phe Asn Tyr Leu Gly Arg Gln Met Pro Arg Glu Ser Cys Glu
                325                 330                 335

Lys Ser Ser Ser Cys Gln Gln His Ser Ser Arg Ser Ser Ser Val Asp
            340                 345                 350

Tyr Ile Leu
        355
```

(2) INFORMATION FOR SEQ ID NO:3:

( i ) SEQUENCE CHARACTERISTICS:
  ( A ) LENGTH: 347 amino acids
  ( B ) TYPE: amino acid
  ( C ) STRANDEDNESS:
  ( D ) TOPOLOGY: linear ( i i ) MOLECULE TYPE: protein ( x i ) SEQUENCE DESCRIPTION: SEQ ID NO:3:

```
Asn Glu Ser Gly Glu Glu Val Thr Thr Phe Phe Asp Tyr Asp Tyr Gly
 1               5                  10                  15
Ala Pro Cys His Lys Phe Asp Val Lys Gln Ile Gly Ala Gln Leu Leu
                20                  25                  30
Pro Pro Leu Tyr Ser Leu Val Phe Ile Phe Gly Phe Val Gly Asn Met
            35                  40                  45
Leu Val Val Leu Ile Leu Ile Asn Cys Lys Lys Leu Lys Cys Leu Thr
    50                  55                  60
Asp Ile Tyr Leu Leu Asn Leu Ala Ile Ser Asp Leu Leu Phe Leu Ile
65                  70                  75                  80
Thr Leu Pro Leu Trp Ala His Ser Ala Ala Asn Glu Trp Val Phe Gly
                85                  90                  95
Asn Ala Met Cys Lys Leu Phe Thr Gly Leu Tyr His Ile Gly Tyr Phe
            100                 105                 110
Gly Gly Ile Phe Phe Ile Ile Leu Thr Ile Asp Arg Tyr Leu Ala
            115                 120                 125
Ile Val His Ala Val Phe Ala Leu Lys Ala Arg Thr Val Thr Phe Gly
    130                 135                 140
Val Val Thr Ser Val Ile Thr Trp Leu Val Ala Val Phe Ala Ser Val
145                 150                 155                 160
Pro Gly Ile Ile Phe Thr Lys Cys Gln Lys Glu Asp Ser Val Tyr Val
                165                 170                 175
Cys Gly Pro Tyr Phe Pro Arg Gly Trp Asn Asn Phe His Thr Ile Met
            180                 185                 190
Arg Asn Ile Leu Gly Leu Val Leu Pro Leu Leu Ile Met Val Ile Cys
            195                 200                 205
Tyr Ser Gly Ile Leu Lys Thr Leu Leu Arg Cys Arg Asn Glu Lys Lys
    210                 215                 220
Arg His Arg Ala Val Arg Val Ile Phe Thr Ile Met Ile Val Tyr Phe
225                 230                 235                 240
Leu Phe Trp Thr Pro Tyr Asn Ile Val Ile Leu Leu Asn Thr Phe Gln
                245                 250                 255
Glu Phe Phe Gly Leu Ser Asn Cys Glu Ser Thr Ser Gln Leu Asp Gln
            260                 265                 270
Ala Thr Gln Val Thr Glu Thr Leu Gly Met Thr His Cys Cys Ile Asn
    275                 280                 285
Pro Ile Ile Tyr Ala Phe Val Gly Glu Lys Phe Arg Arg Tyr Leu Ser
    290                 295                 300
Val Phe Phe Arg Lys His Ile Thr Lys Arg Phe Cys Lys Gln Cys Pro
305                 310                 315                 320
Val Phe Tyr Arg Glu Thr Val Asp Gly Val Thr Ser Thr Asn Thr Pro
                325                 330                 335
Ser Thr Gly Glu Gln Glu Val Ser Ala Gly Leu
            340                 345
```

( 2 ) INFORMATION FOR SEQ ID NO:4:

(i) SEQUENCE CHARACTERISTICS:
  (A) LENGTH: 28 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc = "PRIMER"

(xi) SEQUENCE DESCRIPTION: SEQ ID NO:4:

ACCAGGATCC GCTGCCTTGA TGGATTAT 28

(2) INFORMATION FOR SEQ ID NO:5:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "PRIMER"

(xi) SEQUENCE DESCRIPTION: SEQ ID NO:5:

CTGCTTCTAG AATGCCATTC AAGAAAATGT T 31

(2) INFORMATION FOR SEQ ID NO:6:

(i) SEQUENCE CHARACTERISTICS:
    (A) LENGTH: 55 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "PRIMER"

(xi) SEQUENCE DESCRIPTION: SEQ ID NO:6:

GTGACCGGAT CCCGCTGCCT TGCCGCCATC ATGGATTATA CACTTGACCT CAGTG 55

(2) INFORMATION FOR SEQ ID NO:7:

(i) SEQUENCE CHARACTERISTICS:
    (A) LENGTH: 33 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "PRIMER"

(xi) SEQUENCE DESCRIPTION: SEQ ID NO:7:

TTAATCTAGA GTCTTCATTG ATCCTCCCAA ATG 33